(12) United States Patent
Kikuta et al.

(10) Patent No.: US 7,360,897 B2
(45) Date of Patent: Apr. 22, 2008

(54) FUNDUS EXAMINATION APPARATUS

(75) Inventors: Hisao Kikuta, Sakai (JP); Kazuhiko Ohnuma, Sodegaura (JP); Yasufumi Fukuma, Wako (JP); Takashi Shioiri, Fujisawa (JP); Hidetaka Aeba, Kita-ku (JP)

(73) Assignee: Kabushiki Kaisha Topcon, Tokyo (JP)

( * ) Notice: Subject to any disclaimer, the term of this patent is extended or adjusted under 35 U.S.C. 154(b) by 28 days.

(21) Appl. No.: 11/337,904

(22) Filed: Jan. 24, 2006

(65) Prior Publication Data

US 2006/0164598 A1  Jul. 27, 2006

(30) Foreign Application Priority Data

Jan. 27, 2005  (JP) .............................. 2005-020088

(51) Int. Cl.
*A61B 3/14* (2006.01)
(52) U.S. Cl. ...................... 351/206; 351/205; 351/216; 351/221
(58) Field of Classification Search ................ 351/205, 351/206, 221, 210, 215, 216
See application file for complete search history.

(56) References Cited

U.S. PATENT DOCUMENTS

| | | | |
|---|---|---|---|
| 6,276,798 B1 * | 8/2001 | Gil et al. ..................... | 351/206 |
| 6,704,106 B2 * | 3/2004 | Anderson et al. ........... | 356/367 |
| 2005/0157259 A1 * | 7/2005 | Akita et al. ................. | 351/206 |

FOREIGN PATENT DOCUMENTS

| | | |
|---|---|---|
| JP | 2001-137190 A | 5/2001 |
| JP | 3235853 B2 | 9/2001 |
| JP | 2002-116085 A | 4/2002 |

OTHER PUBLICATIONS

English translation of JP 2002-116085, Publication date Apr. 2002.*
English translation of JP 2001-137190, Publication date May 2001.*

* cited by examiner

*Primary Examiner*—Huy K Mai
(74) *Attorney, Agent, or Firm*—Buchanan Ingersoll & Rooney PC

(57) ABSTRACT

A fundus examination apparatus includes an illumination optical system (20), which illuminates a fundus by fundus illumination light, an imaging optical system (21), which photographs a fundus image based on a polarization property of reflected illumination light, and a picture signal processing device, which processes a signal output from the imaging optical system; and the imaging optical system includes a phase plate array (42) that a plurality of unit constitutional plates (U1) is arranged in a matrix in a plane; each of the unit constitutional plates comprising four or more micro phase plates (44a-44d), a polarizer (43), which polarizes the reflected illumination light passing through the phase plate array (42) into a predetermined polarization direction, and an image pickup device (5a) that a plurality of constitutional units (U2) is arranged in a matrix in a plane; each of the constitutional units comprising four or more pixels (Ga-Gd).

3 Claims, 8 Drawing Sheets relationship between polarization angle $\gamma$ regarding incident radiation (linearly-polarized light) and Stokes' parameter (S0, S1, S2, S3)

relationship between polarization angle $\gamma$ regarding incident radiation (linearly-polarized light) and observation intensity (I0, I1, I2, I3) (when $\delta = 131.8°$)

relationship between polarization angle $\gamma$ regarding incident radiation (linearly-polarized light) and observation intensity (I0, I1, I2, I3) (when $\delta = 60.0°$)

when angle $\alpha$ of advancing phase axis $= \pm 15.1, \pm 54.7$

FUNDUS EXAMINATION APPARATUS

BACKGROUND

1. Field of the Invention

The present invention relates to a fundus examination apparatus suitable for use in a diagnosis of glaucoma, more particularly, to a fundus examination apparatus capable of measuring thickness of a bundle of nerve fibers with high accuracy.

2. Related Art Statement

Conventionally, there has been known a fundus examination apparatus to be mainly used for an eye exam of glaucoma and the like (reference to, for example, Japanese Patent No. 3235853).

The above conventional fundus examination apparatus comprises an illumination optical system, which illuminates a fundus by fundus illumination light of circularly-polarized light, an imaging optical system, which photographs the fundus image of a bundle of nerve fibers of the fundus based on the polarization properties of the illumination light reflected from the fundus by this illumination, and picture signal processing means, which visualize the thickness distribution of the bundle of nerve fibers based on the image photographed by the imaging optical system with a plurality of polarized light states.

Moreover, in the above fundus examination apparatus, the imaging optical system detects the elliptically-polarized light of the fundus reflection light through a polarized light element, and the picture signal processing means obtain the phase distribution regarding the thickness of the bundle of nerve fibers based on the elliptically-polarized light to visualize the thickness distribution of the bundle of nerve fibers.

Furthermore, the imaging optical system includes a TV camera, and the picture signal processing means include a frame memory which stores the image photographed by the TV camera.

There has been also known a fundus examination apparatus capable of measuring thickness of a bundle of nerve fibers. The fundus examination apparatus comprises an illumination optical system, which illuminates a fundus of subject eye by circularly-polarized light, and an imaging optical system in which a CCD camera for imaging the fundus image based on the illumination light reflected from the fundus is disposed. In the above fundus examination apparatus, the imaging surface of the CCD camera is integrally provided with a polarized filter. The polarized filter comprises small plate portions, which are repeatedly disposed. Each of the small plate portions comprises micro polarizing plate portions for resolving the reflected illumination light into linearly-polarized light components, which are orthogonal to each other, and micro polarizing plate portions for resolving the reflected illumination light into linearly-polarized light components having directions intersect ant to both of the linearly-polarized light components (reference to, for example, JP-A-2001-137190). In addition, the micro polarizing plate portions are disposed adjacent to each other.

In this fundus examination apparatus, the micro polarizing plate portion corresponds to each pixel of the CCD camera, and the liner polarized light components having the directions intersect ant to both of the linearly-polarized light components are disposed in the direction at an angle of 45° with respect to both of the linearly-polarized light components.

Furthermore, it is not a fundus examination apparatus, but there has been known a polarized light measuring apparatus which measures polarization properties of an object (reference to, for example, JP-A-2002-116085).

The above polarized light measuring apparatus comprises a condensing optical system which condenses light from an object, a phase plate array in which an unit constitutional plate comprising four micro phase plates, which change the phase state of the light from the condensing optical system and have different angles of the advancing phase axes each other, is arranged in a matrix in a plane, one polarizer which polarizes the light passing through the phase plate array in a predetermined direction, a plurality of light receiving elements (image pick up device), which receives the reflected illumination light uniformed in one polarization direction by passing the polarizer, and arithmetic processing means which calculate Stokes' parameter regarding the light from the object based on the intensity of the reflected illumination light received by the plurality of light receiving elements, respectively.

By the way, in the fundus examination device, polarization properties (double reflection) exist in a bundle of nerve fibers, and reflected light having different velocity each other is generated by the double reflection generated when passing through the bundle of nerve fibers. Accordingly, the fundus examination apparatus utilizes a principle that the difference (phase difference (retardation)) of the velocity generated in the components of the reflected light correlate with the thickness of nerve fibers.

More particularly, as shown in FIG. 1, if illumination is carried out by using an illumination light P0 of circularly-polarized light, the illumination light P0 is reflected by a borderline F between a vitreous body I and a retina (a bundle of nerve fibers) D. Since the reflection by the borderline F is specular reflection, the reflected illumination light P1 maintains the circularly-polarized light.

Next, the illumination light P0 is reflected by a borderline G between the retina D and a pigmented layer G. However, the illumination light P0 becomes elliptically-polarized light by the difference of the velocity of the reflected illumination light P2 when passing through this bundle of nerve fibers. When a bundle of nerve fibers is completely defected, the reflected illumination light P2 maintains the circularly-polarized light, but the reflected illumination light P2 becomes the elliptically-polarized light as the thickness of the bundle of nerve fibers increases, and the oblateness is increased. If a circularly-polarizing plate having a direction same as the reflected illumination light P is provided in the light receiving system, the specular reflection light P1 by the borderline F between the vitreous body I and the retina D becomes the reversely oriented circularly-polarized light; thus, the specular reflection light P1 disappears (reference to Japanese Patent No. 3235853, paragraph [0012] [0013]).

Accordingly, the thickness of a bundle of nerve fibers can be measured by the oblateness of the reflected illumination light P2 of the elliptically-polarized light.

However, the illumination light P may enter into the inside of the pigmented layer G, and may be scattered and reflected by the inside of the pigmented layer G. Therefore, the illumination light P3 scattered and reflected by the inside of the pigmented layer G becomes a non-polarized light state.

The scattered and reflected illumination light P3 is directed to the imaging optical system with the non-polarized state, so the light volume of the scattered and reflected light P3 from the inside of the pigmented layer G is received by the imaging optical system.

Therefore, the light volume of the reflected illumination light P received by the imaging optical system includes the light volume of the scattered and reflected illumination light P3 of non-polarized light from the inside of the pigmented layer G as noise. The light volume of the scattered and reflected illumination light P3 shown in FIG. 1 is added to the reflected illumination light P of elliptically-polarized light shown in FIG. 2 as a noise component, and the reflected illumination light of partially-polarized light enters into the imaging optical system. Consequently, an apparent error is included in the actual thickness of a bundle of nerve fibers.

SUMMARY

Therefore, the present invention has been made in view of the above circumstances, and at least one objective of the present invention is to provide a fundus examination apparatus capable of measuring thickness of a bundle of nerve fibers with high accuracy and low cost without burdening a patient.

To achieve these and other advantages and in accordance with the purpose of the invention, as embodied and broadly described herein, the invention provides a fundus examination apparatus comprises an illumination optical system, which illuminates a fundus by fundus illumination light of circularly-polarized light, an imaging optical system, which photographs a fundus image based on a polarization property of reflected illumination light reflected from the fundus by the fundus illumination light, and a picture signal processing device configured to process a signal output from the imaging optical system, wherein the imaging optical system includes a phase plate array that a plurality of unit constitutional plates is arranged in a matrix in a plane; each of the unit constitutional plates comprising four or more micro phase plates, each of the micro phase plates having a different advancing phase axis each other so as to change a phase state of the reflected illumination light, a polarizer, which polarizes the reflected illumination light passing through the phase plate array into a predetermined polarization direction, and an image pickup device that a plurality of constitutional units is arranged in a matrix in a plane; each of the constitutional units comprising four or more pixels corresponding to each of the micro phase plates, each of the pixels receiving the reflected illumination light that the polarization direction is uniformed in one direction by passing the polarizer, wherein the picture signal processing device is configured to calculate Stokes' parameter of the reflected illumination light from the fundus based on intensity of the reflected illumination light that the polarization direction is uniformed through the polarizer for each of the units, obtain intensity ratio of a polarization component of partially polarized light with respect to the intensity of the reflected illumination light based on the calculation results of the Stokes' parameter, and obtain thickness of a bundle of nerve fibers of the fundus by correcting the Stokes' parameter with the ratio.

According to one embodiment of the present invention, an angle of each of advancing phase axes of the four micro phase plates with respect to the polarization direction of the polarizer comprises four different angles, $\alpha 0$, $\alpha 1$, $\alpha 2$, $\alpha 3$, respectively, and the four different angles, $\alpha 0$, $\alpha 1$, $\alpha 2$, $\alpha 3$ are $-51.7°$, $-15.1°$, $+15.1°$, $+51.7°$, or $-74.9°$, $-38.3°$, $+38.3°$, $+74.9°$, respectively.

According to one embodiment of the present invention, retardation $\delta$ of the micro phase plate is $131.8°$.

The present application is based on, and claims priority from, Japanese Patent Application No. 2005-20088, filed on Jan. 27, 2005, the contents of which are hereby incorporated by reference herein in its entirety.

DETAILED DESCRIPTION OF THE PREFERRED EMBODIMENT

Hereinafter, an embodiment of a fundus examination apparatus according to the present invention will be described with reference to the accompanying drawings.

Figure 1:
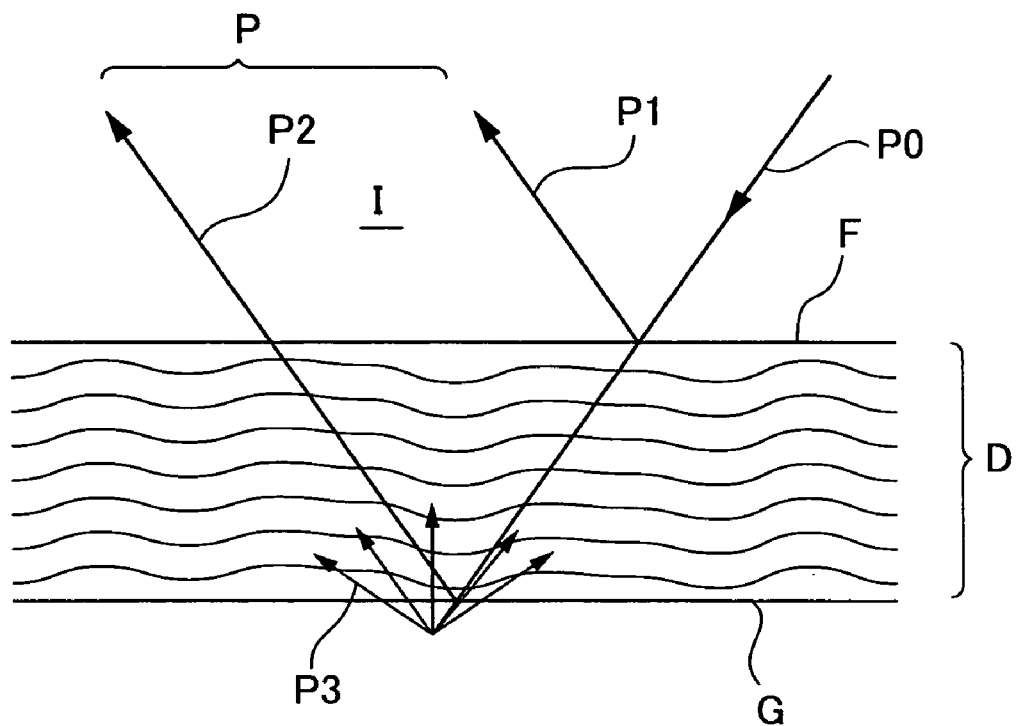
FIG. 1 is a schematic diagram showing reflection states from a fundus.
Figure 2:
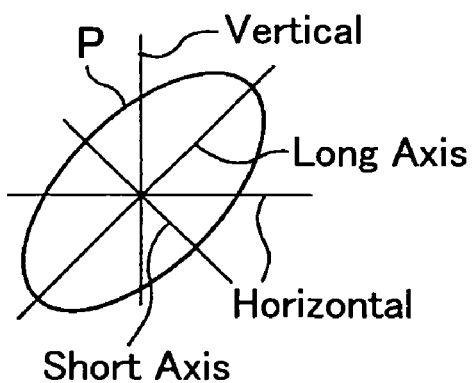
FIG. 2 is a schematic diagram showing one example of a polarized state of reflected illumination light from a fundus.
Figure 3:
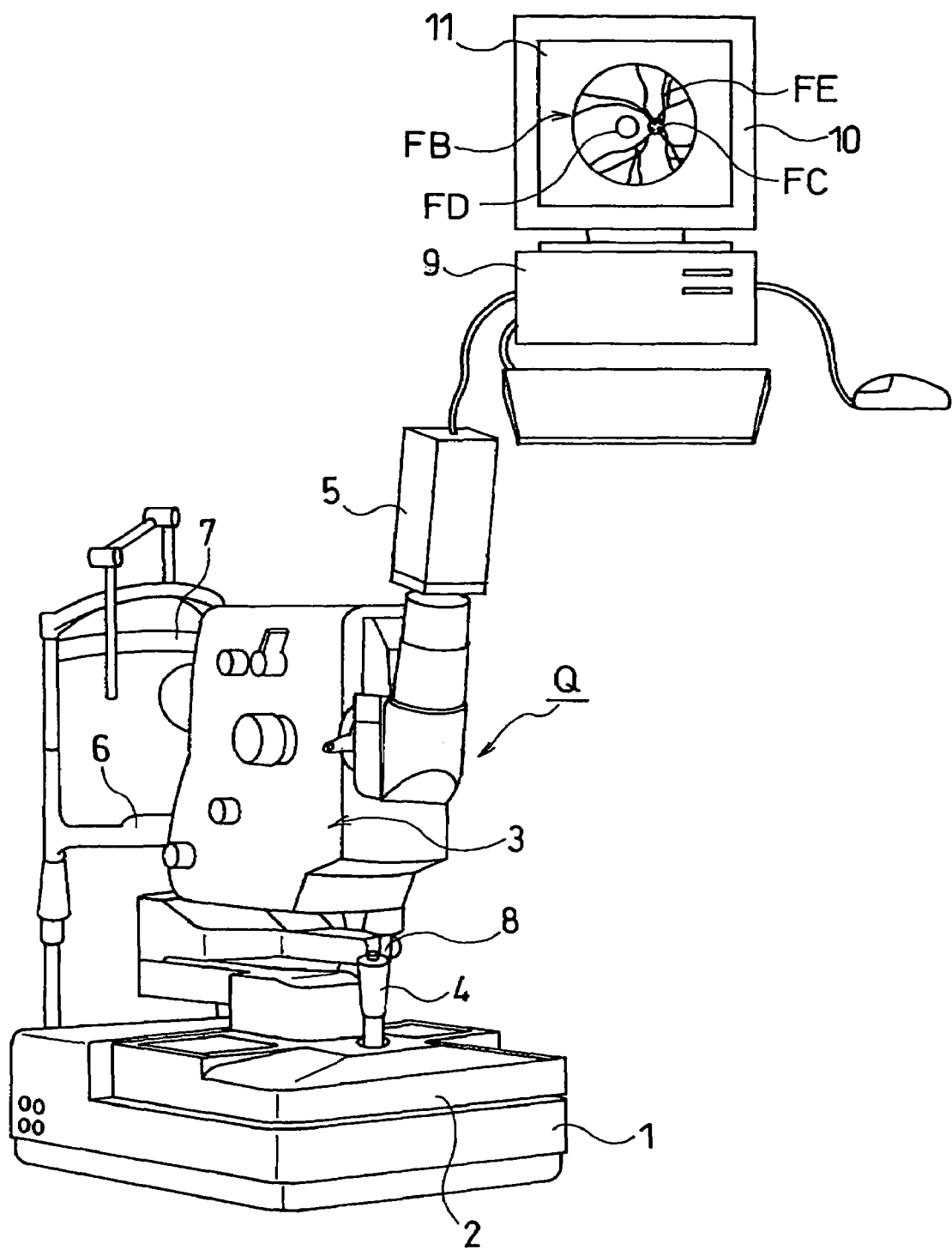
FIG. 3 is an external view of a fundus camera of a fundus examination apparatus according to the present invention.

FIG. 3 shows an example of a fundus camera Q used for the fundus examination apparatus of the present invention. FIG. 3 shows a base 1, mount 2, body 3, joystick 4, CCD camera 5, chin receiver 6, and forehead pad 7.

When imaging a fundus image by the fundus camera Q, a patent puts his chin on the chin receiver 6 and presses his forehead against the forehead pad 7, and the patent is fixed to a predetermined direction by an internal fixation lamp, for example. With this state, when a photographing switch 8 is operated, a fundus of subject eye is illuminated by the after-mentioned illumination optical system, and then the fundus image is imaged by the CCD camera 5 of the after-mentioned imaging optical system (light receiving system).

The CCD camera 5 is connected to, for example, a personal computer 9, which constitutes a part of the fundus examination apparatus. The fundus image is stored in, for example, a frame memory (image storing device) of the personal computer 9.

An image displaying monitor 10 is connected to the personal computer 9. A fundus image FB stored in the frame memory is displayed on a screen 11 by operation devices such as a mouse and keyboard. In this case, reference numeral FC denotes papillae, reference numeral FD denotes a macular area and reference numeral FE denotes a blood vessel.

Figure 4:
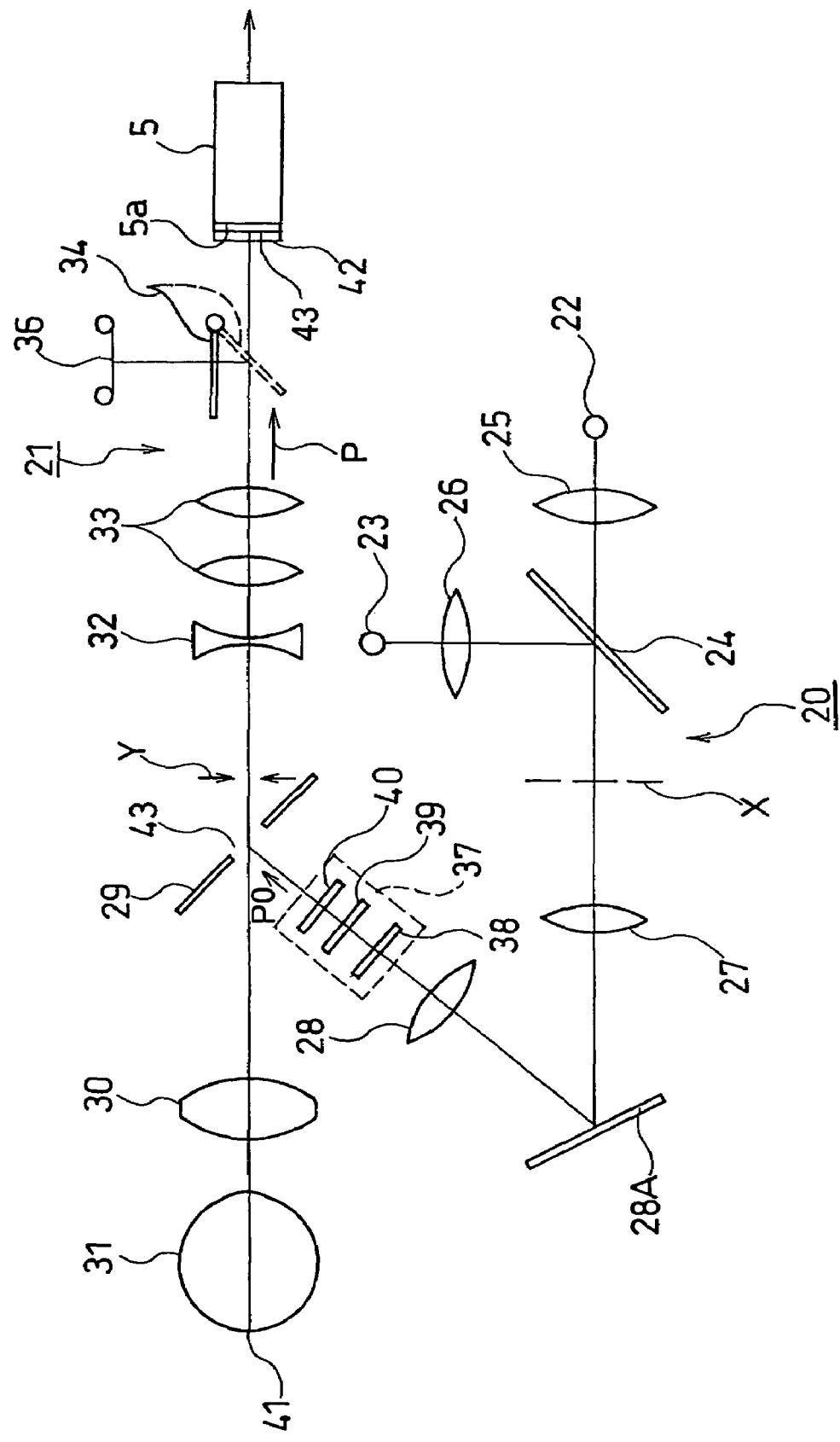
FIG. 4 is a view illustrating an optical system of the fundus camera shown in FIG. 3.

FIG. 4 illustrates an optical system of the fundus camera Q. FIG. 4 shows an illumination optical system 20 and an imaging optical system 21. The illumination optical system 20 includes a xenon lamp 22 and a halogen lamp 23. The xenon lamp 22 and the halogen lamp 23 are disposed in conjugated positions with respect to a half mirror 24. The xenon lamp 22 and the halogen lamp 23 are relayed to the vicinity of a ring-shaped aperture stop X by condenser lenses 25, 26.

The ring-shaped aperture stop X is relayed to the vicinity of a pupil of a subject eye 31 via a relay lens 27, total reflection mirror 28A, relay lens 28, perforated mirror 29 and objective lens 30.

The imaging optical system 21 includes an objective lens 30 facing to the subject eye 31, the perforated mirror 29, a focused lens 32, a relay lens 33, a flip turn mirror 34, the CCD camera 5, and a photographic film 36. Reference numeral 5a denotes an imaging surface of the CCD camera 5. The photographic film 36 and the imaging surface 5a are conjugated with respect to the flip turn mirror 34.

When photographing is carried out by the photographic film, the flip turn mirror 34 is inserted into the optical path between the relay lens 33 and the CCD camera 5 as shown by the dotted line, and is left from the optical path when observing or photographing by the CCD camera 5.

A polarizing unit 37 is insertably and detachably disposed between the relay lens 28 and perforated mirror 29 in the optical path of the illumination optical system 20. The polarizing unit 37 comprises a green filter (or interference filter) 38, a polarized filter 39 having a liner polarization property, and a ¼ wavelength plate 40. The polarizing unit 37 is left from the optical path of the illumination optical system 20 when observing the fundus 41 of the subject eye 31.

Figure 5:
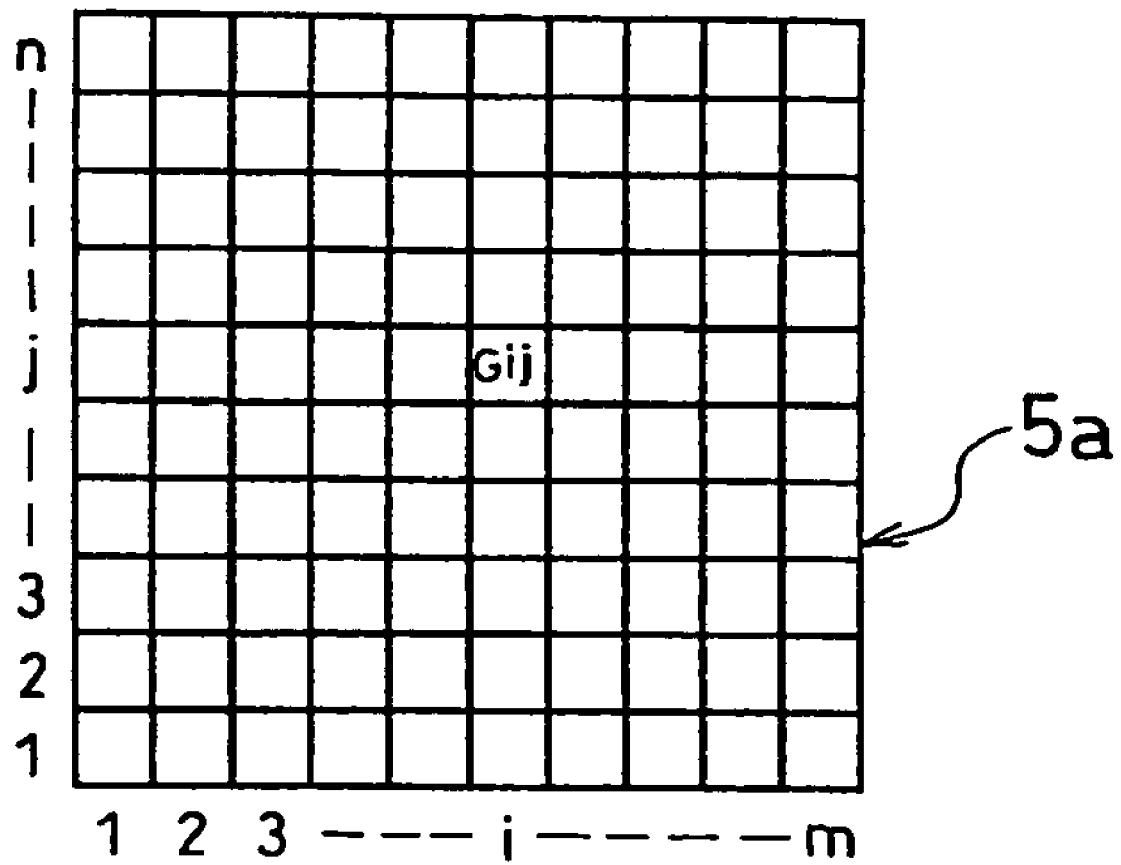
FIG. 5 is a plan view showing an imaging surface of a CCD camera illustrated in FIG. 4.

An image pick up device (imaging surface) 5a of the CCD camera 5 comprises a number of pixels Gij (i=1, 2, . . . , m ; j=1, 2, . . . , n) as shown in FIG. 5. The front plane of the imaging surface 5a is provided with a phase plate array 42 and a polarizing plate 43 as shown in FIG. 4. The phase plate array 42 plays a role of changing the phase state of the reflected illumination light P from the fundus passing through the focused lens 32 and relay lens 33 and heading to the CCD camera 5.

The polarizing plate 43 is disposed between the phase plate array 42 and the CCD camera 5. The reflected illumination light P passing through the polarizing plate 43 is received by the CCD camera 5.

The receiving output of the CCD camera 5 is input to the personal computer 9. The personal computer 9 also has a function as the after-mentioned picture signal processing device. The personal computer 9 is used to calculate Stokes' parameter regarding the light from the fundus based on the light receiving intensity for each pixel Gij of the CCD camera 5.

Figure 6:
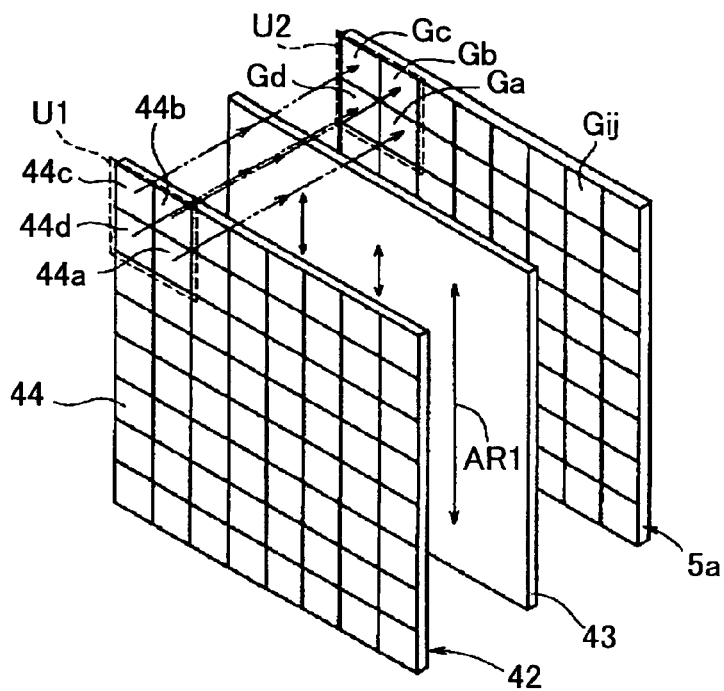
FIG. 6 is an enlarged perspective view illustrating relationship among a phase plate array, a polarizing plate and an imaging surface shown in FIG. 3.

The phase plate array 42 includes a plurality of micro phase plates 44 disposed in a matrix in a plane, as shown in FIG. 6. A total of four micro phase plates (for example 44a-44d) arranged in a matrix in a plane two by two in the plurality of micro phase plates 44 constructs one unit constitutional plate (constitutional unit U1). Moreover, the constitutional unit U1 is repeatedly arranged in a matrix in a plane.

The polarizing plate 43 plays a role as a polarizer which polarizes incident radiation to a predetermined direction AR1, and one polarizing plate 43 is used. The polarizing plate 43 has one size which is enough for the entire phase plate array 42. The phase plate array 42 and the polarizing plate 43 are pasted each other to be integrally manufactured.

Since the polarization direction of the polarizing plate 43 has the same direction with respect to every micro phase plates 44, it is not necessary to separately dispose a polarizing plate having a different polarization direction in accordance with each phase plate 44. For example, it is sufficient to dispose a single polarizing plate 43 having a size enough for the entire phase plate array 42.

In addition, when a plurality of polarizing plates is separately disposed in accordance with each of the micro phase plates 44, the polarization directions of the plurality of polarizing plates are the same. Therefore, it is not necessary to precisely align the position of each micro phase plate 44 and the position of each polarizing plate.

Each of the pixels Gij of the CCD camera 5 forms a constitutional unit U2 in which a total of four pixels Ga-Gd is arranged in a matrix in a plane. The CCD camera 5 can be a light receiving element array in which those constitutional units U2 are repeatedly arranged in a matrix in a plane. CMOS can be used as the light receiving element array instead of using the CCD camera 5. The frame rate of the CMOS is 1 ms (millisecond) while the frame rate of the CCD camera 5 is 30 ms (millisecond); thus, it is preferable for high speed photographing to use the CMOS as the light receiving element array.

The four pixels Ga-Gd contained in each constitutional unit U2 respectively receive the light passing through each of the phase plates 44a-44d of the corresponding constitutional unit U1. More particularly, the reflected illumination light P from the fundus passes through each of the micro phase plates 44a-44d, and passes through the polarizing plate 43, and then enters to each pixel Gij of each constitutional unit U2 with an uniformed polarization direction.

In the constitutional unit U1, each angle α of advancing phase axes of the four micro phase plates 44a-44d is different each other. Each of the advancing phase axes of the four micro phase plates 44a-44d includes a different angle α1, α2, α3, α4, respectively.

Figure 7A:
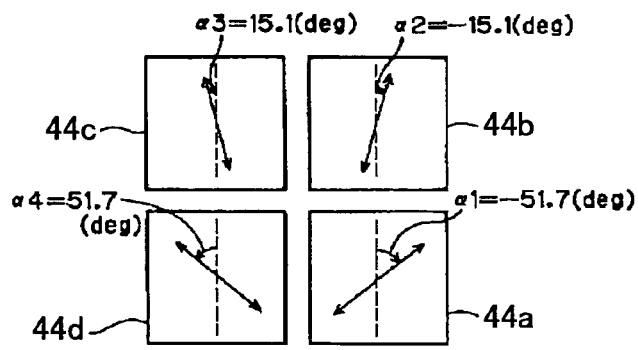
FIG. 7 A is an explanation view illustrating advancing phase axes of micro phase plates of a constitutional unit U1 with respect to the polarizing plate shown in FIG. 6, and showing when an angle of each advancing axis is $-51.7°$, $-15.1°$, $+15.1°$, $+51.7°$.
FIG. 7B is an explanation view illustrating advancing phase axes of micro phase plates of a constitutional unit U1 with respect to the polarizing plate shown in FIG. 6, and showing when an angle of each advancing axis is $-74.9°$, $-38.3°$, $+38.3°$, $+74.9°$.
Figure 7B:
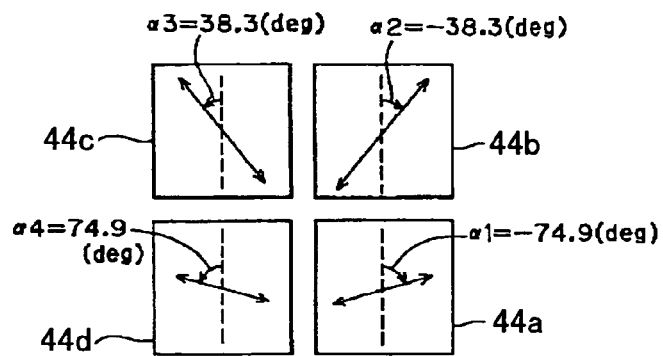

FIG. 7 shows a view showing the directions of the advancing phase axes of the four micro phase plates 44a-44d. FIG. 7A illustrates when the angles α1-α4 of the advancing phase axes of the micro phase plates 44a-44d with respect to the polarization direction AR1 of the polarizing plate 43 are −51.7°, −15.1°, +15.1°, +51.7°, respectively. FIG. 7B illustrates when these angles α1-α4 are −74.9°, −38.3°, +38.3°, +74.9°, respectively. In addition, in FIGS. 7A, 7B, each of the directions of the advancing phase axes of four micro phase plates 44a-44d is shown by an arrow, and each of the advancing phase axes has an angle that the counterclockwise direction with respect to the polarization direction AR1 is the positive direction. The details of the manufacturing method of each micro phase plate 44 are described in JP-A-2002-116085; thus, the explanation will be omitted.

Figure 8:
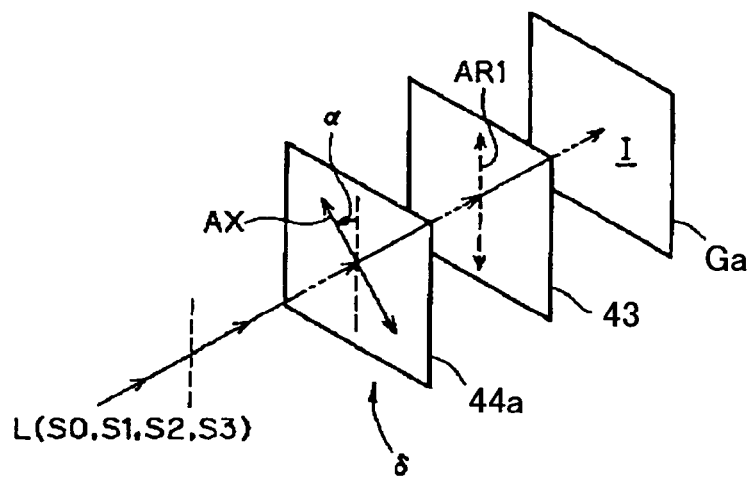
FIG. 8 is a view illustrating relationship among one micro phase plate, a polarization plate and one pixel.

Next, a measurement principle will be explained with reference to FIG. 8. FIG. 8 is a schematic diagram showing the relationship among one micro phase plate 44a, one polarizing plate 43 and one pixel Ga.

In this case, as shown in FIG. 8, when the light L having Stokes' parameter S0, S1, S2, S3 of polarization properties is received by the pixel Ga by passing through the micro phase plate 44a and the polarizing plate 43, the intensity I of the received light is expressed by the following equation 1.

$$I(\alpha, \delta) = \frac{1}{2} \cdot \left\{ S0 + S1 \cdot \left(1 - 2 \cdot \sin^2 2\alpha \cdot \sin^2 \frac{\delta}{2}\right) + \right.$$
$$\left. S2 \cdot \sin 4\alpha \cdot \sin^2 \frac{\delta}{2} - S3 \cdot \sin 2\alpha \cdot \sin \delta \right\}$$
Equation 1

Figure 9:
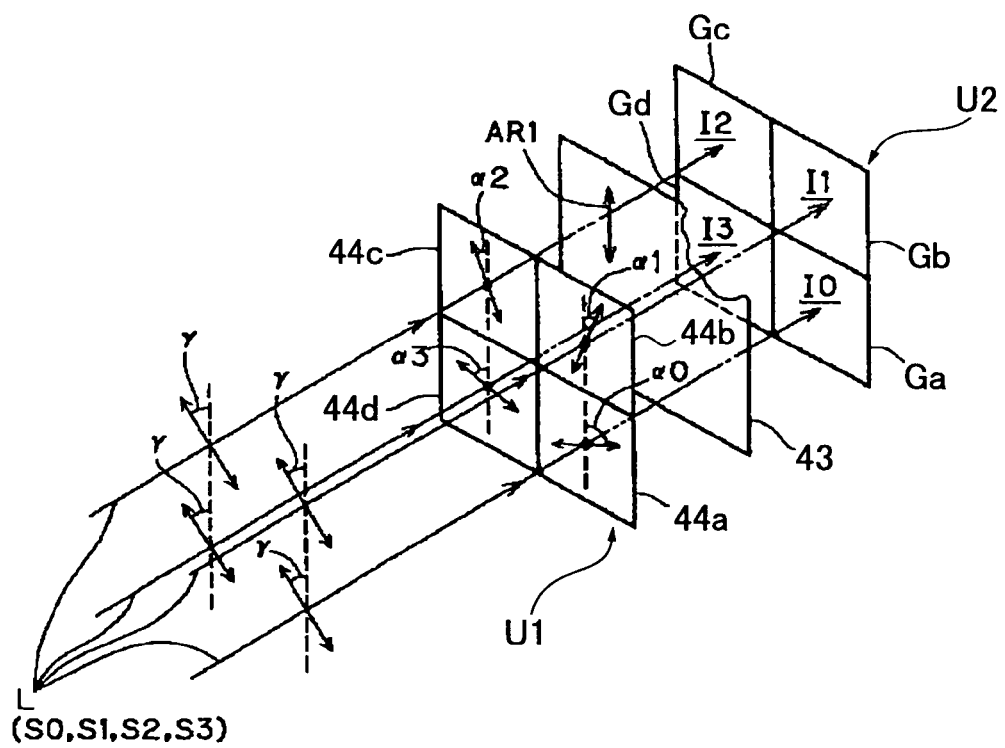
FIG. 9 is a view showing a state that linearly-polarized light having each angle $\gamma$ is entered into the constitutional unit U1, one polarizing plate and the constitutional unit U2.

Where, α is an angle of the advancing phase axis AX of the micro phase plate 44a with respect to the polarization direction AR1 of the polarizing plate 43, and δ is retardation of the micro phase plate 44a. In addition, the similar relationship is realized for the light passing through each of the four phase plates 44a-44d. FIG. 9 is a schematic diagram showing the relationship between the polarizing plate 43 and the pixels Ga-Gd for the four micro phase plates 44a-44d.

As shown in FIG. 9, light intensity received by the pixels Ga-Gd is I0, I1, I2, I3, respectively. In this case, the relational expression of the equation 1 is realized for each angle α=α1, α2, α3, α4, and those are integrated by a determinant and can be expressed by the following equation 2.

$$I = AS \qquad \text{Equation 2}$$

Where, ([ ]T represent transposed matrix.)

$$\begin{cases} I = [I0 \; I1 \; I2 \; I3]^T \\ S = [S0 \; S1 \; S2 \; S3]^T \\ A = \frac{1}{2} \begin{bmatrix} 1 & \{1 - 2 \cdot \sin^2(2 \cdot \alpha 0) \cdot \sin^2 \frac{\delta}{2}\} & \sin(4 \cdot \alpha 0) \cdot \sin^2 \frac{\delta}{2} & -\sin(2 \cdot \alpha 0) \cdot \sin \delta \\ 1 & \{1 - 2 \cdot \sin^2(2 \cdot \alpha 1) \cdot \sin^2 \frac{\delta}{2}\} & \sin(4 \cdot \alpha 1) \cdot \sin^2 \frac{\delta}{2} & -\sin(2 \cdot \alpha 1) \cdot \sin \delta \\ 1 & \{1 - 2 \cdot \sin^2(2 \cdot \alpha 2) \cdot \sin^2 \frac{\delta}{2}\} & \sin(4 \cdot \alpha 2) \cdot \sin^2 \frac{\delta}{2} & -\sin(2 \cdot \alpha 2) \cdot \sin \delta \\ 1 & \{1 - 2 \cdot \sin^2(2 \cdot \alpha 3) \cdot \sin^2 \frac{\delta}{2}\} & \sin(4 \cdot \alpha 3) \cdot \sin^2 \frac{\delta}{2} & -\sin(2 \cdot \alpha 3) \cdot \sin \delta \end{bmatrix} \end{cases}$$

In addition, reference numeral S denotes a vector with Stokes' parameter S0, S1, S2, S3 as an element, and the vector I is a vector with the light intensity (observation intensity) I0, I1, I2, I3 received by each pixel Ga-Gd as an element. Moreover, the matrix A is a coefficient matrix with each angle α1, α2, α3, α4, and retardation δ as a parameter.

In this case, when the inverse matrix of the matrix A exists, the vector S regarding Stokes' parameter can be expressed by the following equation 3 with the vector I regarding the observation intensity.

$$S = A^{-1}I(=GI) \qquad \text{Equation 3}$$

In addition, if the inverse matrix of the matrix A is represented by using symbol G, each element of the matrix G can be expressed by using the equation 4.

$$A^{-1} = G = \begin{bmatrix} A1 & B1 & C1 & D1 \\ A2 & B2 & C2 & D2 \\ A3 & B3 & C3 & D3 \\ A4 & B4 & C4 & D4 \end{bmatrix} \qquad \text{Equation 4}$$

Therefore, by using the equation 3, Stokes' parameter S0, S1, S2, S3 can be obtained based on the observation intensity I0, I1, I2, I3 of each pixel Ga-Gd.

In fact, it is preferable to consider manufacturing errors of the phase plate array 42 and the polarizing plate 43, a feature of each pixel Gij, and the like, but hereinafter, analysis of polarization properties will be explained under an optically idealized condition.

Figure 10:
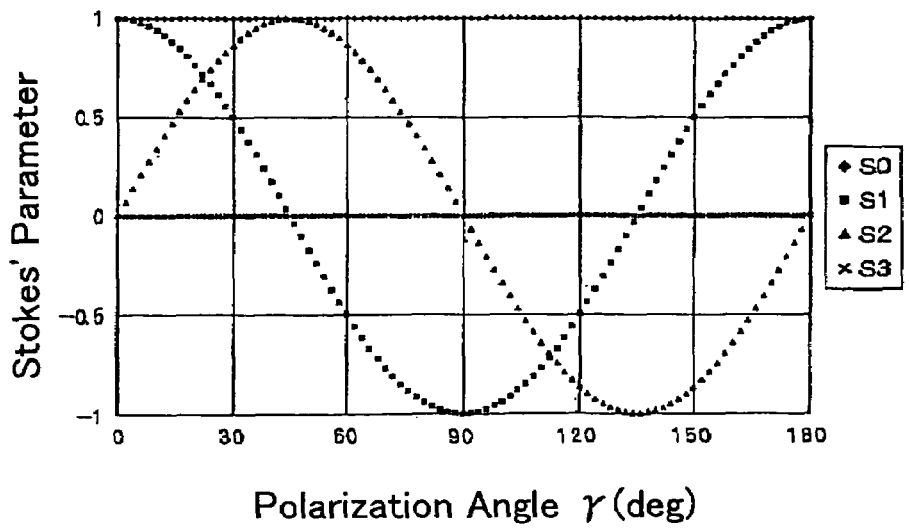
FIG. 10 is a graph showing relationship between linearly-polarized light having an angle $\gamma$ and Stokes' parameter.
Figure 11:
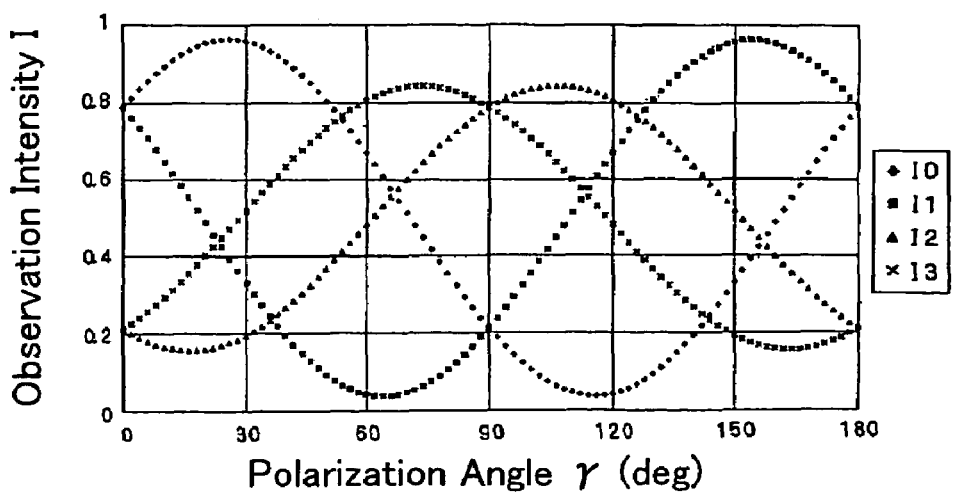
FIG. 11 is a graph illustrating relationship between light of linearly-polarized light having an angle $\gamma$ and Stokes' parameter, when the retardation is $131.8°$.
Figure 12:
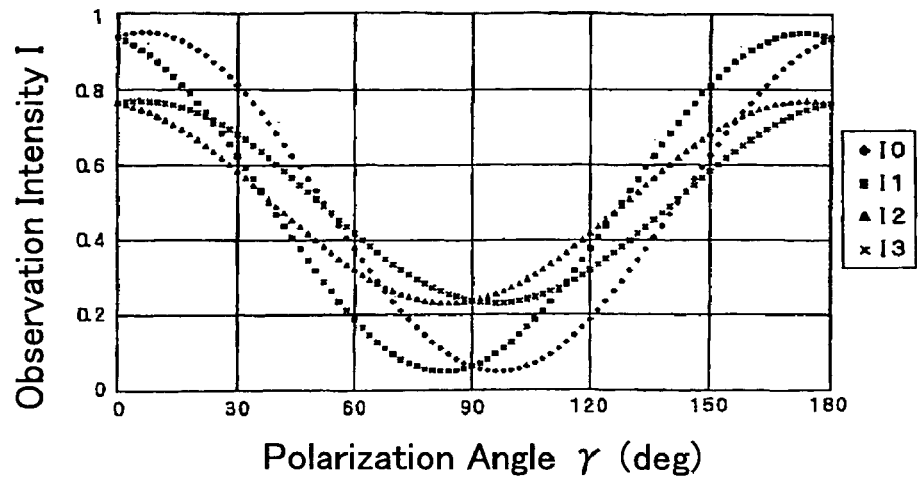
FIG. 12 is a graph illustrating relationship between light of linearly-polarized light having an angle $\gamma$ and Stokes' parameter, when the retardation is $60.0°$.

FIGS. 9 to 12 are views explaining the measurement processing of Stokes' parameter S0, S1, S2, S3 of linearly-polarized light. FIG. 9 is a view illustrating when the light of the linearly-polarized light state having a predetermined angle γ with respect to the polarization direction AR1 of the polarizing plate 43 enters to each of the micro phase plates 44a-44d, the polarizing plate 43 and each of the pixels Ga-Gd shown in FIG. 8. In addition, FIG. 10 is a graph showing the relationship between the linearly-polarized light having the angle γ and Stokes' parameter S0, S1, S2, S3. Furthermore, FIGS. 11, 12 show the relationship between the linearly-polarized light having the angle γ and the observation intensity I0, I1, I2, I3 received by each pixel Ga-Gd, respectively. FIG. 11 shows when the retardation is δ=131.8°, and FIG. 12 shows when the retardation is δ=60.0°.

As shown in FIG. 9, the linearly-polarized light polarized to the direction of a predetermined angle γ with respect to the polarization direction AR1 of the polarizing plate 43 has Stokes' parameter S0, S1, S2, S3 corresponding to the linearly-polarized light state. According to the graph of FIG. 10, it is known that, for example, when γ=0°, (S0, S1, S2, S3)=(1, 1, 0, 0), and γ=90°, (S0, S1, S2, S3)=(1, −1, 0, 0).

In addition, according to the graph of FIG. 11, theoretical figures of the observation intensity I0, I1, I2, I3 when the linearly-polarized light polarized in the direction of the angle γ is observed by each of the four phase plates 44a-44d can be obtained.

For example, the light of the linearly-polarized light having γ=0° is observed as the light having each of the observation intensity (I0, I1, I2, I3)=(0.8, 0.08, 0.2, 02) in each of the four phase plates 44a-44d.

As stated above, the linearly-polarized light having the predetermined angle γ has the corresponding Stokes' parameter S0, S1, S2, S3, and is received by each of the micro phase plates 44a-44d as the light of observation intensity I0, I1, I2, I3, respectively. The relationship between this Stokes' parameter and the observation intensity is represented by the equation 2.

Contrary, by using the equation 3 which is the inverse transform equation of equation 2, Stokes' parameter S0, S1, S2, S3 of the observation light can be obtained based on the observation intensity I0, I1, I2, I3 of the actual measurement values. This calculation is performed by using the personal computer 9. In this case, the explanation was given for linearly-polarized light, but the similar relationship can be obtained for elliptically-polarized light.

Stokes' parameter representing polarization properties of light from a micro area of a fundus can be obtained by using the unit which puts together the four micro phase plates 44a-44d and the four pixels Ga-Gd corresponding to those plates. The polarization properties for the micro area of the fundus can be measured by using the observation intensity of light in the area for the constitutional unit U2 of four pixels Ga-Gd.

This fundus examination apparatus has a plurality of constitutional units U1 and a plurality of constitutional units U2. Each of the four pixels Ga-Gd in the constitutional unit U2 can simultaneously receive the reflected illumination light P from a plurality of micro areas of the fundus through each of the micro phase plates 44a-44d and one polarizing plate 43. Therefore, polarization properties of each of micro areas of a fundus can be simultaneously measured.

By the way, a polarized light component and a non-polarized light component a remixed in the reflected illumination light P from the fundus, and the reflected illumination light P is partially polarized.

The amplitude of the partially-polarized light is adopted as the sum of x component and y component of the electric field E of non-polarized light, which changes temporally and in random manner, ax, ay, and the amplitude of completely-polarized light component, Ax, Ay.

In this regard, the electric field components Ex (z, t), Ey (z, t) are expressed by the following equations.

Electric filed component $Ex(z,t)=Ax \cos(\omega t - kz + \delta x)$

Electric filed component $Ey(z,t)=Ay \cos(\omega t - kz + \delta y)$

Where, k is a propagation constant in the traveling direction of light (z direction), and δx, δy are initial phases, respectively.

In case of partially-polarized light, Stokes' parameter S0, S1, S2, S3 can be expressed by the following formulas with time average symbols < >.

$S0 = A_x^2 + A_y^2 + a_x^2 + a_y^2 + <2A_x a_x + 2A_y a_y>$ $S1 = A_x^2 - A_y^2 + <a_x^2 - a_y^2 + 2A_x a_x - 2A_y a_y>$ $S2 = 2A_x A_x \cos \delta + 2<(A_x a_y + a_x A_y + a_x a_y) \cos \delta>$ $S3 = 2A_x A_x \sin \delta + 2<(A_x a_y + a_x A_y + a_x a_y) \sin \delta>$ With respect to the partially-polarized light, if the time average is calculated, the portion of the time average symbol, < >, becomes 0, and is omitted; thus, the above Stokes' parameter becomes as follows.

$S0 = A_x^2 + A_y^2 + a_x^2 + a_y^2$ $S1 = A_x^2 - A_y^2$ $S2 = 2A_x A_x \cos \delta$ $S3 = 2A_x A_x \sin \delta$ In this case, Stokes' parameter S0 corresponds to the light intensity I. In the non-polarized light, Ax, Ay is 0 by the definition, so S1, S2, S3 are all 0.

On the contrary, S1, S2, S3 does not have a value for the non-polarized component; thus, the light intensity of completely-polarized light can be expressed by $S0^2 = S1^2 + S2^2 + S3^2$.

At the same time, the light intensity of partially-polarized light is expressed by $S0^2 \geq S1^2 + S2^2 + S3^2$.

If the intensity of partially-polarized light is S0, Stokes' parameter of the completely-polarized light can be expressed by using the following expression 5 and Stokes' parameter of the non-polarized light can be expressed by using the following expression 6.

$((S_1^2 + S_2^2 + S_3^2)^{1/2}, S_1, S_2, S_3)$      Expression 5

$((S_0^2 - (S_1^2 + S_2^2 + S_3^2))^{1/2}, 0, 0, 0)$      Expression 6

Accordingly, when the ratio of the intensity of completely-polarized light, $(S1^2 + S2^2 + S3^2)^2$ with respect to the total of the intensity of reflected illumination light, S0 is defined as a polarization degree V, the following equation 7 can be obtained.

$$V = \frac{\sqrt{S_1^2 + S_2^2 + S_3^2}}{S_0}$$      Equation 7

Therefore, Stokes' parameter of reflected illumination light from the fundus 41 is calculated by the personal computer 9 based on the intensity of reflected illumination light P in which the polarization direction is aligned through one polarizer for each unit, and the ratio of the intensity of completely-polarized light with respect to the intensity of the reflected illumination light P is obtained based on the calculation result of Stokes' parameter, and then the thickness of a bundle of nerve fibers of fundus can be obtained by correcting the Stokes' parameter with this ratio.

More particularly, the four micro phase plates 44a-44d and the four pixels Ga-Gd corresponding to the plates are repeatedly arranged in a matrix in a plane. Therefore, the light having polarization properties from the plane of the fundus, which has two dimensional spread, can be continuously received as the image, which has two dimensional spread, by the CCD camera 5; thus, the in-plane distribution regarding the polarization properties can be preciously measured in a short time.

In addition, according the fundus examination apparatus, the fundus reflection light P3 of non-polarized light can be minimized by the following means.

According to the equation 3, an error variation vector, ΔS when measuring Stokes' parameter can be expressed by using the following equation 8 with an error variation vector, ΔI regarding an error of observation intensity.

$$\Delta S = A^{-1} \Delta I \left( \text{Where,} \begin{cases} \Delta S = [\Delta S0 \ \Delta S1 \ \Delta S2 \ \Delta S3]^T \\ \Delta I = [\Delta I0 \ \Delta I1 \ \Delta I2 \ \Delta I3]^T \end{cases} \right)$$    Equation 8

Where, if variations in the intensity of vector I are the same level, and a standard deviation σ for each element ΔI0, ΔI1, ΔI2, ΔI3 of the vector ΔI is equal, a condition for minimizing this error variation can be expressed that an evaluation value ρ defined by the following equation 9 becomes minimum.

$$\rho \triangleq \sigma \cdot \sqrt{\sum_i (Ai^2 + Bi^2 + Ci^2 + Di^2)} \quad \text{Equation 9}$$

More particular, the problem of measurement error in the fundus examination apparatus results in the optimization problem of an evaluation value ρ.

In this equation 9, Ai, Bi, Ci, Di are values, which express each component of the matrix G (the inverse matrix of matrix A) shown in the equation 4. Each value, Ai, Bi, Ci, Di is a value having α0, α1, α2, α3, δ as a parameter, respectively. Therefore, the combination of each value, Ai, Bi, Ci, Di which determines an evaluation value ρ is expressed as the combination of each value, α0, α1, α2, α3, δ. More particular, the measurement error can be a lowered value by obtaining a preferable combination of each value (α0, α1, α2, α3, δ).

Two combinations (α0, α1, α2, α3, δ)=(−51.7°, −15.1°, +15.1°, +51.7°, +131.8°), and (α0, α1, α2, α3, δ)=(−74.9°, −38.3°, +38.3°, +74.9°) regarding each value which minimizes the evaluation value ρ in the formula 9 can be obtained by solving the optimization problem regarding the evaluation value ρ by using an numerical calculation and the like. Where, an angle α (α0, α1, α2, α3) is obtained within −90°≦α≦+90°, a retardation δ is obtained within 0°≦δ≦180°. More particularly, those two combinations are the optimal solutions of the optimization problem, and the angles α of those two combinations are the angles shown in FIGS. 7A, 7B.

Figure 13:
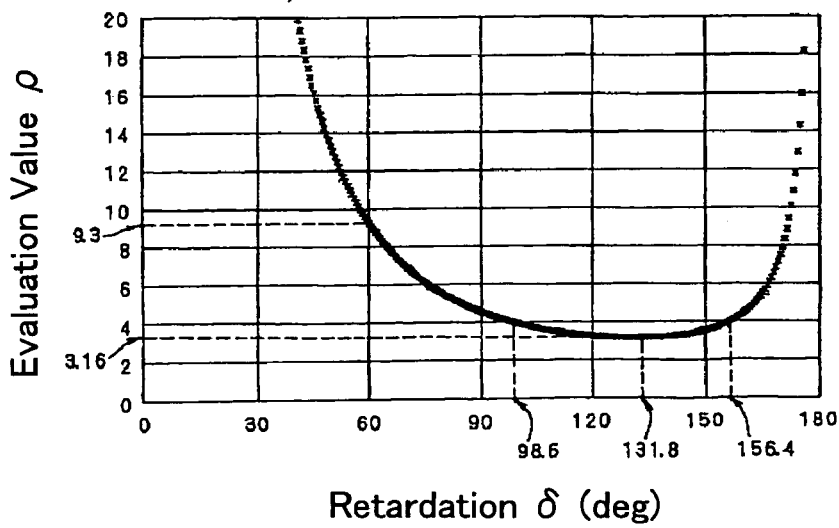
FIG. 13 is a graph showing relationship between evaluation values when an angle $\alpha$ of advancing phase axis is $+15.1°$, $-15.1°$, $+54.7°$, $-54.7°$ and retardation.

FIG. 13 is a graph showing the relationship between retardations δ and evaluation values ρ when the combination shown in FIG. 7A is used. The horizontal axis of this graph shows retardations δ, and the vertical axis of this graph shows evaluation values ρ. In addition, the same graph is shown, when the combination shown in FIG. 7B is used.

As shown in FIG. 13, when the retardation δ is 131.8°, the evaluation value ρ becomes the minimum value. Accordingly, when each of the advancing axes of the four micro phase plates 44a-44d has the angle shown in FIG. 7A with respect to the polarization direction of the polarizing plate 43, and the retardation δ is 131.8°, the evaluation value ρ is minimized; thus, the measurement error of Stokes' parameter can be minimized.

By the way, FIG. 11 shows the relationship between a polarization angle γ of linearly-polarized light and each of the observation intensity, I0, I1, I2, I3 when the retardation δ is 131.8°. FIG. 12 shows the relationship between a polarization angle γ of linearly-polarized light and each of the observation intensity, I0, I1, I2, I3 when the retardation δ is 60.0°.

As shown in FIG. 12, when the retardation δ is 60.0°, a difference between each of the observation intensity I0, I1, I2, I3 in the four micro phase plates 44a-44d is relatively small for the light having either polarization angle γ. Namely, all of the observation intensity of light passing through each of the micro phase plates 44a-44d has a similar value. Therefore, when such observation intensity is used, the measurement error increases.

On contrary, as shown in FIG. 11, when the retardation δ is 131.8°, a difference between each of the observation intensity I0, I1, I2, I3 in the four micro phase plates 44a-44d is relatively large for the light having either polarization angle γ. Accordingly, when such observation intensity is used, the measurement error can be reduced.

As stated above, when the retardation δ is 131.8°, a difference degree of each observation intensity I0, I1, I2, I3 is relatively large compared with when the retardation δ is 60.0°. Accordingly, the measurement error can be reduced when the retardation δ is 131.8°.

This relationship is shown in FIG. 13, when the retardation δ is 131.8°, the evaluation value ρ is 3.16 (minimum value), while the retardation δ is 60.0°, the evaluation value ρ is 9.3.

As stated above, in the embodiment of the present invention, four micro phase plates are used for one unit, but five or more micro phase plates can be used for one unit. For a pixel corresponding to the micro phase plate, five or more pixel can be used for one unit.

In this case, an error can be further reduced by obtaining four Stokes' parameter with the least-square method.

According to the present invention, the reflected illumination light from the fundus is received and photographed with the polarized state that the polarization direction is uniformed in a predetermined polarization direction, i.e., a single direction, not with a plurality of polarized states. Therefore, thickness of a bundle of nerve fibers can be measured with high accuracy without burdening a patient.

It will be obvious to those having skill in the art that many changes may be made in the above-described details of the preferred embodiment of the present invention. The scope of the present invention, therefore, should be determined by the following claims.

What is claimed is:

1. A fundus examination apparatus, comprising:
   an illumination optical system which illuminates a fundus by fundus illumination light of circularly-polarized light;
   an imaging optical system which photographs a fundus image based on a polarization property of reflected illumination light reflected from the fundus by the fundus illumination light; and
   a picture signal processing device configured to process a signal output from the imaging optical system, wherein the imaging optical system includes:
   a phase plate array having a plurality of unit constitutional plates that are arranged in a matrix in a plane; each of the unit constitutional plates comprising four or more micro phase plates, each of the micro phase plates having a different advancing phase axis with respect to each other so as to change a phase state of the reflected illumination light;
   a polarizer which polarizes the reflected illumination light passing through the phase plate array into a predetermined polarization direction, and
   an image pickup device that includes a plurality of constitutional units arranged in a matrix in a plane; each of the constitutional units comprising four or more pixels corresponding to each of the micro phase plates, each of the pixels receiving the reflected illumination light that the polarization direction has uniformed in one direction by passing the polarizer, wherein
   the picture signal processing device includes a calculator which calculates Stokes' parameter of the reflected illumination light from the fundus based on an intensity of the reflected illumination light that the polarization direction has uniformed through the polarizer for each of the constitutional units and obtains an intensity ratio of a polarization component of partially polarized light with respect to the intensity of the reflected illumination light based on the calculation results of the Stokes' parameter in order to obtain a thickness of a bundle of nerve fibers of the fundus while minimizing an apparent thickness resulting from existence of a pigmented layer by correcting the Stokes' parameter with the ratio.

2. The fundus examination apparatus according to claim 1, wherein an angle of each of advancing phase axes of the four micro phase plates with respect to the polarization direction of the polarizer comprises four different angles, $\alpha 0$, $\alpha 1$, $\alpha 2$, $\alpha 3$, respectively, and the four different angles, $\alpha 0$, $\alpha 1$, $\alpha 2$, $\alpha 3$ are $-51.7°$, $-15.1°$, $+15.1°$, $+51.7°$, or $-74.9°$, $+38.3°$, $+38.3°$, $+74.9°$, respectively.

3. The fundus examination apparatus according to claim 1, wherein retardation $\delta$ of the micro phase plate is $131.8°$.

* * * * *